(12) United States Patent
Fischer et al.

(10) Patent No.: US 8,629,227 B2
(45) Date of Patent: Jan. 14, 2014

(54) MODIFIED POLYVINYLLACTAMS

(75) Inventors: Frank Fischer, Kirchheim (DE); Ludger Wegmann, Ludwigshafen (DE); Michael Ehle, Ludwigshafen (DE); Stephan Bauer, Hochheim (DE); Harald Meyer, Wachenheim (DE); Son Nguyen Kim, Hemsbach (DE)

(73) Assignee: BASF SE, Ludwigshaften (DE)

( * ) Notice: Subject to any disclaimer, the term of this patent is extended or adjusted under 35 U.S.C. 154(b) by 162 days.

(21) Appl. No.: 13/133,171

(22) PCT Filed: Dec. 2, 2009

(86) PCT No.: PCT/EP2009/066188
§ 371 (c)(1), (2), (4) Date: Jun. 7, 2011

(87) PCT Pub. No.: WO2010/066613
PCT Pub. Date: Jun. 17, 2010

(65) Prior Publication Data
US 2011/0248428 A1 Oct. 13, 2011

(30) Foreign Application Priority Data
Dec. 12, 2008 (EP) .................... 08171502

(51) Int. Cl.
*C08F 226/06* (2006.01)
*C08F 226/10* (2006.01)
*C08F 12/32* (2006.01)

(52) U.S. Cl.
USPC ......................... 526/264; 526/316

(58) Field of Classification Search
USPC .................................. 526/264, 316
See application file for complete search history.

(56) References Cited

U.S. PATENT DOCUMENTS

| 3,992,356 | A | 11/1976 | Jacquet et al. |
| 4,499,175 | A | 2/1985 | Curtis et al. |
| 5,128,386 | A | 7/1992 | Rehmer et al. |
| 6,465,525 | B1 | 10/2002 | Guire et al. |
| 6,555,587 | B1 | 4/2003 | Guire et al. |
| 6,858,295 | B2 * | 2/2005 | Diehl et al. .................. 428/343 |
| 7,091,296 | B2 * | 8/2006 | Meyer et al. .................. 526/319 |
| 2005/0080213 | A1 | 4/2005 | Meyer et al. |
| 2005/0147919 | A1 * | 7/2005 | Kunz et al. .................... 430/311 |

FOREIGN PATENT DOCUMENTS

| EP | 0 246 848 | 11/1987 |
| EP | 1 478 671 | 11/2004 |
| GB | 2 109 392 | 6/1983 |
| WO | 99 47176 | 9/1999 |
| WO | 03 064061 | 8/2003 |
| WO | 03 070792 | 8/2003 |

OTHER PUBLICATIONS

International Search Report issued Apr. 21, 2010 in PCT/EP09/066188 filed Dec. 2, 2009.

* cited by examiner

*Primary Examiner* — Ling Choi
*Assistant Examiner* — David L Miller
(74) *Attorney, Agent, or Firm* — Oblon, Spivak, McClelland, Maier & Neustadt, L.L.P.

(57) ABSTRACT

Modified polyvinyllactams and their use.

17 Claims, No Drawings

MODIFIED POLYVINYLLACTAMS

The present invention provides a copolymer comprising in copolymerized form 0.01% to 20% by weight of at least one ethylenically unsaturated compound of the general formula (I) [monomers A], 50% to 99.99% by weight of at least one N-vinyllactam of the general formula (VII) [monomers B], and 0% to 49.99% by weight of at least one further ethylenically unsaturated compound [monomers C] which differs from the monomers A and monomers B, the total amounts of monomers A, B and C summing to 100% by weight (total monomer amount), with R—(C=O)—R$^1$ as formula (I), where R is a straight-chain $C_1$-$C_4$ alkyl radical, a branched, optionally substituted $C_3$ or $C_4$ alkyl radical, an aryl radical or the radical R$^1$, and R$^1$ is the radical

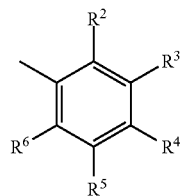

where the radicals R$^2$ to R$^6$ are like or different from one another and are hydrogen, alkyl, aryl, OH, $OCH_3$, $OC_2H_5$, SH, $SCH_3$, $SC_2H_5$, F, Cl, Br, CN, $CO_2H$, $CO_2$alkyl, $CO_2$aryl, $CF_3$, $N(alkyl)_2$, N(alkyl)(aryl), $N(aryl)_2$, $N^+(alkyl)3A^-$, $N^+H(alkyl)_2A^-$, where $A^-$ is the anion of an acid, and at least one but not more than three of the radicals R$^2$ to R$^6$ is or are one of the radicals —O—C(=O)—O—X—Z—C(=O)—C(Y)=CH$_2$, or  formula (II)

—O—C(=O)—O—X—Z—CH=CH$_2$, or  formula (III)

—Z—C(Y)=CH$_2$, or  formula (IV)

—C(=O)—O—X—Z—C(=O)—C(Y)=CH$_2$, or  formula (V)

—C(=O)—O—X—Z—CH=CH$_2$  formula (VI)

in which

X is a divalent, optionally substituted alkylene radical —(CH$_2$)$_m$—, a radical

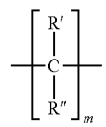

with m=1 to 10, in which R' and R" are like or different from one another and are hydrogen, alkyl, aryl, $CO_2H$, $CO_2CH_3$ or $CO_2C_2H_5$, a perfluorinated alkylene radical —(CF$_2$)$_m$— with m=1 to 10, an oxaalkylene radical of the type —(CH$_2$)$_n$—O—(CH$_2$)$_p$—, a perfluorinated oxaalkylene radical of the type —(CF$_2$)$_n$—O—(CF$_2$)$_p$— with n=1 to 5 and p=1 to 5, or an optionally perfluorinated polyoxaalkylene radical having 2 to 20 oxygen atoms which are joined to one another via at least one —CH$_2$—, —CF$_2$— or —CH$_2$—CH(CH$_3$)-group, or are an alkylene radical of the type —(CH$_2$)$_a$—O—CO—O(CH$_2$)$_b$—, —(CH$_2$)$_a$—O—CO—NH—(CH$_2$)$_b$—, —(CH$_2$)$_a$—NH—CO—O—(CH$_2$)$_b$—, —(CH$_2$)$_a$—CO—(CH$_2$)$_b$— or —(CH$_2$)$_a$—O—CO—(CH$_2$)$_b$— with a=1 to 10 and b=1 to 10, a phenylene radical which is optionally substituted by alkyl, OH, $OCH_3$, $OC_2H_5$, SH, $SCH_3$, $SC_2H_5$, Cl, F, $N(alkyl)_2$ or $N(CH_3)C_6H_5$ in o-, m- and/or p-position, or a cycloalkylene radical having 5 to 10 carbon atoms or a (bis)methylenecycloalkylene radical having 6 to 12 carbon atoms, Y is hydrogen, alkyl or aryl, and Z is O or NY, or, if R is an aryl radical, one of the radicals R$^2$ or R$^6$ may be a sulfur atom which connects the aryl radical R in o-position to R$^1$, and with

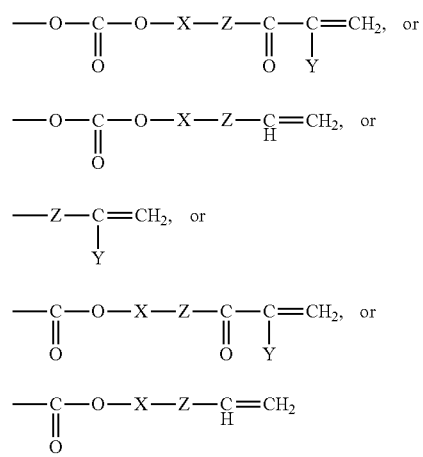

$CH_2=CH—N—C=O$ as formula (VII), where

P and Q: independently of one another are hydrogen and/or alkyl and d: is an integer from 2 to 8.

The present invention further provides a process for preparing the copolymer of the invention, and also provides for its use in a very wide variety of fields of application, especially for pore formation in and permanent hydrophilicization of polymer membranes.

Copolymers comprising groups that are sensitive to UV radiation are familiar to the skilled worker (in this regard see, for example, EP-A 246848, EP-A 377191, EP-A 377199 or EP-A 1478671). Copolymers of this kind are generally prepared by polymerizing monomers which carry a radiation-sensitive group with other monomers which are composed substantially of hydrophobic monomer units, such as alkyl esters of α,β-monoethylenically unsaturated $C_3$ to $C_6$ monocarboxylic or dicarboxylic acids, vinylaromatic compounds, alkyl esters of vinyl alcohol, nitriles of α,β-monoethylenically unsaturated carboxylic acid, or conjugated $C_{4-8}$ dienes. In this kind of polymerization, hydrophilic monomers, especially α,β-monoethylenically unsaturated $C_3$ to $C_6$ monocarboxylic or dicarboxylic acids, and their amides, are used only in minor amounts. Generally speaking, the resulting polymers are insoluble in water or else soluble in water only to a greatly restricted extent, and so cannot be used in a large number of fields of application.

It was an object of the present invention, therefore, to provide copolymers which comprise radiation-sensitive groups and which are composed substantially of hydrophilic monomer units and therefore have good solubility in water.

Surprisingly the object has been achieved by means of the copolymers defined at the outset.

In the context of this specification "alkyl" stands for linear or branched $C_1$ to $C_{24}$ alkyl radicals, preferably $C_1$ to $C_{10}$ alkyl radicals, and more particularly for $C_1$ to $C_4$ alkyl radicals and "aryl" stands for $C_6$, $C_{10}$ or $C_{14}$ monocyclic or polycyclic aromatic radicals, such as phenyl, 1- or 2-naphthyl, 1-, 2- or 9-anthracenyl, and 1-, 2- or 9-phenanthryl, which if appropriate may additionally be substituted by one or more substituents, such as, in particular, hydroxyl, dialkylamino, halogen, such as fluorine, chlorine, and bromine, alkyloxy, such as methoxy, ethoxy and n-butoxy, or alkoxycarbonyl, such as methoxycarbonyl, ethoxycarbonyl, and n-butoxycarbonyl. Preferred alkyl radicals are methyl, ethyl, n-propyl, isopropyl, n-butyl, isobutyl, tert-butyl or 2-ethoxyethyl, and preferred aryl radicals are phenyl, p-chlorophenyl, and tolyl.

Monomers A used are compounds of the general formula (I) where

R is a straight-chain $C_1$-$C_4$ alkyl radical, preferably methyl, ethyl or n-propyl, a branched, optionally substituted $C_3$ or $C_4$ alkyl radical, such as isopropyl, 2-hydroxyisopropyl, 2-dimethylaminoisopropyl, 2-morpholinoisopropyl or tert-butyl, an aryl radical, such as phenyl, o-, m- or p-tolyl, 1- or 2-naphthyl, for example, or the radical $R^1$, and $R^1$ is the radical

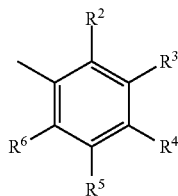

where the radicals $R^2$ to $R^6$ are like or different from one another and are hydrogen, alkyl, aryl, OH, $OCH_3$, $OC_2H_5$, SH, $SCH_3$, $SC_2H_5$, F, Cl, Br, CN, $CO_2H$, $CO_2$alkyl, $CO_2$aryl, $CF_3$, $N(alkyl)_2$, $N(alkyl)(aryl)$, $N(aryl)_2$, $N^+(alkyl)_3A^-$, $N^+H(alkyl)_2A^-$, where $A^-$ is the anion of an acid, for example, $Cl^-$, $SO_4^{2-}$, $PO_4^{3-}$, $CH_3CO_2^-$, $BF_4^-$, $CF_3SO_3^-$, $SbF_6^-$, $AsF_6^-$ or $PF_6^-$, and at least one but not more than three of the radicals $R^2$ to $R^6$ is or are one of the radicals

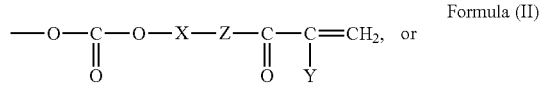  Formula (II)

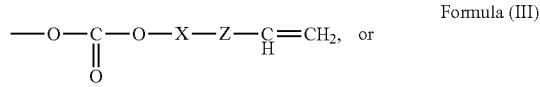  Formula (III)

  Formula (IV)

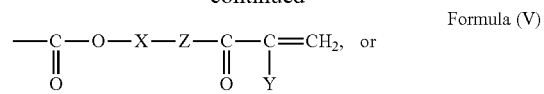  Formula (V)

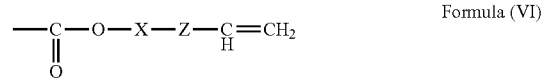  Formula (VI)

in which

X is a divalent, optionally substituted alkylene radical $-(CH_2)_m-$, a radical

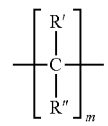

with m=1 to 10, in which R' and R" are like or different from one another and are hydrogen, alkyl, aryl, $CO_2H$, $CO_2CH_3$ or $CO_2C_2H_5$, a perfluorinated alkylene radical $-(CF_2)_m-$ with m=1 to 10, preferably a perfluoroethylene radical, an oxaalkylene radical of the type $-(CH_2)_n-O-(CH_2)_p-$, a perfluorinated oxaalkylene radical of the type $-(CF_2)_n-O-(CF_2)_p-$ with n=1 to 5 and p=1 to 5, such as tetrafluoroethylene, for example, or an optionally perfluorinated polyoxaalkylene radical having 2 to 20 oxygen atoms which are joined to one another via at least one $-CH_2-$, $-CF_2-$ or $-CH_2-CH(CH_3)-$ group, or are an alkylene radical of the type $-(CH_2)_a-O-CO-O(CH_2)_b-$, $-(CH_2)_a-O-CO-NH-(CH_2)_b-$, $-(CH_2)_a-NH-CO-O-(CH_2)_b-$, $-(CH_2)_a-CO-(CH_2)_b-$ or $-(CH_2)_a-O-CO-(CH_2)_b-$ with a=1 to 10 and b=1 to 10, a phenylene radical which is optionally substituted by alkyl, OH, $OCH_3$, $OC_2H_5$, SH, $SCH_3$, $SC_2H_5$, Cl, F, $N(alkyl)_2$ or $N(CH_3)C_6H_5$ in o-, m- and/or p-position, or a cycloalkylene radical having 5 to 10 carbon atoms or a (bis)methylenecycloalkylene radical having 6 to 12 carbon atoms, Y is hydrogen, alkyl or aryl, and Z is O or NY, or, if R is an aryl radical, one of the radicals $R^2$ or $R^6$ may be a sulfur atom which connects the aryl radical R in o-position to $R^1$.

The preparation of these monomers A is known to the skilled worker from, for example, EP-A 377191 [at least one of the radicals $R^2$ to $R^6$ is the structural element of the formulae (II) and (III)], EP-A 1478671 [at least one of the radicals $R^2$ to $R^6$ is the structural element of the formula (IV)]. The compounds corresponding to the monomers A that are disclosed in these specifications are to be regarded, by virtue of this express reference, as part of the present specification. Furthermore, monomers A of this kind can be obtained, for example, as commercial products Uvercryl® P 36 from Sigma-Aldrich Chemie GmbH or Ebecryl® P 36 from Cytec Surface Specialties Inc. [at least one of the radicals $R^2$ to $R^6$ is the structural element of the formula (V)]. Preferred as monomers A are the compounds, corresponding to the monomers A, of examples 19 to 34 of EP-A 377191, 4-vinyloxybenzophenone of EP-A 1478671, and also the aforementioned commercial products Uvercryl® P 36 and Ebecryl® P 36. Particularly preferred as monomers A are compounds of the general formula (I) in which R is phenyl,
R$^2$, R$^3$, R$^5$, and R$^6$ are hydrogen, and
R$^4$ is a group of the formula (II) in which
X is (CH$_2$)$_4$,
Y is hydrogen, and
Z is O,
or in which
R is phenyl,
R$^2$, R$^3$, R$^5$, and R$^6$ are hydrogen, and
R$^4$ is a group of the formula (IV) in which
Y is hydrogen and
Z is O,
or in which
R is p-chlorophenyl,
R$^2$, R$^3$, R$^5$, and R$^6$ are hydrogen, and
R$^4$ is a group of the formula (V) in which
X is (CH$_2$)$_2$,
Y is hydrogen, and
Z is O.

The total amount of monomers A in the copolymer of the invention is 0.01% to 20% by weight, preferably 0.1% to 10% by weight, and with particular preference 0.1% to 5% by weight in copolymerized form.

Monomers B used are N-vinyllactams of the general formula (VII)

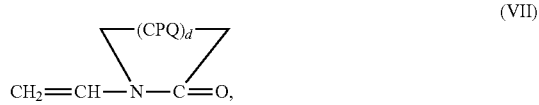

(VII)

where
P and Q: independently of one another are hydrogen and/or alkyl and
d: is an integer from 2 to 8.

P and Q here may independently of one another be hydrogen and/or C$_1$-C$_8$ alkyl, such as methyl, ethyl, n-propyl, isopropyl, n-butyl, isobutyl, tert-butyl and also n-pentyl, n-hexyl, n-heptyl or n-octyl and their isomeric alkyl groups. Preferred as P and Q are hydrogen and methyl. Hydrogen is particularly preferred. Frequently the N-vinyllactam (VII) comprises no methyl group or only one methyl group in total.

In accordance with the invention d is an integer from 2 to 8, frequently 3, 4, 5, 6 and 7. In particular d is 3 and 5.

Examples of monomers B are the N-vinyl derivatives of the following lactams: 2-pyrrolidone, 2-piperidone, ε-caprolactam, and their alkyl derivatives, such as, for example, 3-methyl-2-pyrrolidone, 4-methyl-2-pyrrolidone, 5-methyl-2-pyrrolidone, 3-ethyl-2-pyrrolidone, 3-propyl-2-pyrrolidone, 3-butyl-2-pyrrolidone, 3,3-dimethyl-2-pyrrolidone, 3,5-dimethyl-2-pyrrolidone, 5,5-dimethyl-2-pyrrolidone, 3,3,5-trimethyl-2-pyrrolidone, 5-methyl-5-ethyl-2-pyrrolidone, 3,4,5-trimethyl-2-pyrrolidone, 3-methyl-2-piperidone, 4-methyl-2-piperidone, 5-methyl-2-piperidone, 6-methyl-2-piperidone, 6-ethyl-2-piperidone, 3,5-dimethyl-2-piperidone, 4,4-dimethyl-2-piperidone, 3-methyl-ε-caprolactam, 4-methyl-ε-caprolactam, 5-methyl-ε-caprolactam, 6-methyl-ε-caprolactam, 7-methyl-ε-caprolactam, 3-ethyl-ε-caprolactam, 3-propyl-ε-caprolactam, 3-butyl-ε-caprolactam, 3,3-dimethyl-ε-caprolactam or 7,7-dimethyl-ε-caprolactam. It will be appreciated that there may also be two or more monomers B present in copolymerized form. Used with particular advantage are N-vinylpyrrolidone and/or N-vinylcaprolactam, with N-vinylpyrrolidone being particularly preferred.

The total amount of monomers B in the copolymer of the invention is 50% to 99.99% by weight, preferably 90% to 99.9% by weight, and with particular preference 95% to 99.9% by weight in copolymerized form.

Suitable monomers C include all those ethylenically unsaturated compounds which are simply free-radically copolymerizable with the monomers A and B, such as, for example, vinylaromatic monomers, such as styrene, α-methylstyrene, o-chlorostyrene or vinyltoluenes, vinyl halides, such as vinyl chloride or vinylidene chloride, esters of vinyl alcohol and monocarboxylic acids having 1 to 18C atoms, such as vinyl acetate, vinyl propionate, vinyl-n-butyrate, vinyl neodecanoate, vinyl laurate, and vinyl stearate, esters of α,β-monoethylenically unsaturated monocarboxylic and dicarboxylic acids having preferably 3 to 6C atoms, such as, more particularly, acrylic acid, methacrylic acid, maleic acid, fumaric acid, and itaconic acid, with alkanols having generally 1 to 12, preferably 1 to 8, and more particularly 1 to 4C atoms, such as, in particular, methyl, ethyl, n-butyl, isobutyl, pentyl, hexyl, heptyl, octyl, nonyl, decyl, and 2-ethylhexyl acrylate and methacrylate, dimethyl or di-n-butyl fumarate and maleate, nitriles of α,β-monoethylenically unsaturated carboxylic acids, such as acrylonitrile, methacrylonitrile, fumaronitrile, and maleonitrile, ethers of vinyl alcohol and alcohols having 1 to 18 carbon atoms, such as, for example, n-butyl, cyclohexyl, dodecyl, ethyl, 4-hydroxybutyl or octadecyl vinyl ether, and also C$_{4-8}$ conjugated dienes, such as 1,3-butadiene(butadiene) and isoprene. As a general rule these monomers in water under standard conditions [20° C., 1 atm (absolute)] have only a moderate to low solubility. Normally the aforementioned monomers C are employed only as modifying monomers in amounts of ≤10%, preferably ≤5%, and with particular preference ≤3%, by weight, based in each case on the total amount of monomers C. With more particular preference, however, no such monomers C at all are used.

Monomers C which exhibit enhanced water solubility under the aforementioned conditions are those which comprise either at least one carboxylic or sulfonic acid group or its corresponding anion and/or at least one amino, amido, ureido, or N-heterocyclic group and/or ammonium derivatives thereof that are alkylated or protonated on the nitrogen. Mention may be made, by way of example, of acrylic acid, methacrylic acid, fumaric acid, maleic acid, and itaconic acid, vinylsulfonic acid, 2-acrylamido-2-methylpropanesulfonic acid, styrenesulfonic acid, and the water-soluble salts thereof, advantageously the alkali metal salts or ammonium salts thereof, acrylamide and methacrylamide, and also 2-vinylpyridine, 4-vinylpyridine, 2-vinylimidazole, 2-(N,N-dimethylamino)ethyl acrylate, 2-(N,N-dimethylamino)ethyl methacrylate, 2-(N,N-diethylamino)ethyl acrylate, 2-(N,N-diethylamino)ethyl methacrylate, 2-(N-tert-butylamino) ethyl methacrylate, N-(3-N',N'-dimethylaminopropyl) methacrylamide, and 2-(1-imidazolin-2-onyl)ethyl methacrylate. The stated monomers generally form the principal monomers, which, based on the total amount of monomers C, account for a fraction of ≥50%, preferably ≥80%, and with particular preference ≥90%, by weight, or even form the total amount of the monomers C. With more particular preference, however, no such monomers C at all are used.

Monomers C which customarily enhance the internal strength of the films of a polymer matrix normally have at least one hydroxyl, at least one epoxy and/or at least one carbonyl group or at least two nonconjugated ethylenically unsaturated double bonds. Examples of monomers C of this kind are monomers containing two vinyl radicals, monomers containing two vinylidene radicals, and monomers containing two alkenyl radicals. Particularly advantageous in this context are the diesters of dihydric alcohols with α,β-monoethylenically unsaturated monocarboxylic acids, among which acrylic and methacrylic acid are preferred. Examples of monomers of this kind containing two nonconjugated ethylenically unsaturated double bonds are alkylene glycol diacrylates and dimethacrylates, such as ethylene glycol diacrylate, 1,2-propylene glycol diacrylate, 1,3-propylene glycol diacrylate, 1,3-butylene glycol diacrylate, 1,4-butylene glycol diacrylates and ethylene glycol dimethacrylate, 1,2-propylene glycol dimethacrylate, 1,3-propylene glycol dimethacrylate, 1,3-butylene glycol dimethacrylate, 1,4-butylene glycol dimethacrylate, and also divinylbenzene, N,N'-divinylethyleneurea, vinyl methacrylate, vinyl acrylate, allyl methacrylate, allyl acrylate, diallyl maleate, diallyl fumarate, methylenebisacrylamide, cyclopentadienyl acrylate, triallyl cyanurate or triallyl isocyanurate. Advantageously it is also possible to use hydroxyl-functionalized acrylic or methacrylic acid alkyl esters, such as, for example, 2-hydroxyethyl, 2-hydroxypropyl or 4-hydroxybutyl acrylate or methacrylate. Frequently the aforementioned crosslinking monomers C are used in amounts of ≤10% by weight, but preferably in amounts of ≤3% by weight, based in each case on the total amount of monomers C. With more particular preference, however, no such monomers C at all are used.

The total amount of monomers C in the copolymer of the invention is 0% to 49.99% by weight, preferably 0% to 10% by weight, and with particular preference 0% to 5% by weight in copolymerized form.

The preparation of the copolymers of the invention is uncritical and is accomplished by polymerization, preferably by free-radical polymerization of the monomers A and B and also, if appropriate, C. The free-radical polymerization of the monomers A and B and also, if appropriate, C may take place in the form of a bulk polymerization or in the form of a solution polymerization.

In the preparation of the copolymers of the invention it is possible in each case, if appropriate, to charge the polymerization vessel with a portion or the whole amount of monomers A and B and also, if appropriate, C. An alternative possibility is to meter in each case the total amount or, if appropriate, the remainder of monomers A and B and also, if appropriate, C in during the polymerization reaction. The respective total amount or, if appropriate, the remainder of monomers A and B and also, if appropriate, C may in that case be metered into the polymerization vessel discontinuously in one or more portions or continuously with constant or changing volume flow rates. It will be appreciated that the invention also comprises copolymers which are obtained by a staged or gradient regime. With advantage at least portions of the monomers are included in the initial charge.

With advantage the free-radical polymerization takes place in the form of a solution polymerization in—for example—water or an organic solvent. The free-radically initiated solution polymerization of the monomers A, B and/or C takes place preferably in a protic or an aprotic organic solvent, particular preference being given to protic solvents. Suitable protic organic solvents include all organic solvents which under polymerization conditions comprise at least one ionizable proton in the molecule. Examples of solvents of this kind are preferably all linear, branched or cyclic $C_1$ to $C_8$ alcohols, such as, for example, methanol, ethanol, n-propanol, isopropanol, 1-butanol, 2-butanol, 2-methylpropan-1-ol, 2-methylpropan-2-ol, n-pentanol, and also isomeric compounds, n-hexanol and also isomeric compounds, n-heptanol and also isomeric compounds or n-octanol and also isomeric compounds, ethylene glycol, propylene glycol, but also cyclopentanol, cyclohexanol, 1,2-cyclopentanediol or 1,2-cyclohexanediol, and also the alkoxylated derivatives, especially ethoxylated and/or propoxylated derivatives, of the aforementioned alcohols. Suitable aprotic organic solvents include all organic solvents which under polymerization conditions comprise no ionizable proton in the molecule. Examples of solvents of this kind are aromatic hydrocarbons, such as toluene, o-, m-, p-xylene and isomer mixtures, and also ethylbenzene, linear or cyclic aliphatic hydrocarbons, such as pentane, hexane, heptane, octane, nonane, dodecane, cyclohexane, cyclooctane, methylcyclohexane, and also mixtures of the aforementioned hydrocarbons and benzine fractions which comprise no polymerizable monomers, aliphatic or aromatic halogenated hydrocarbons, such as chloroform, carbon tetrachloride, hexachloroethane, dichloroethane, tetrachloroethane, chlorobenzene, and also liquid $C_1$ and/or $C_2$ hydrofluorochlorocarbons, aliphatic $C_2$ to $C_5$ nitriles, such as acetonitrile, propionitrile, butyronitrile or valeronitrile, linear or cyclic aliphatic $C_3$ to $C_7$ ketones, such as acetone, methyl ethyl ketone, methyl isobutyl ketone, 2- and/or 3-hexanone, 2-, 3- and/or 4-heptanone, cyclopentanone, cyclohexanone, linear or cyclic aliphatic ethers, such as diisopropyl ether, 1,3- or 1,4-dioxane, tetrahydrofuran or ethylene glycol dimethyl ether, carbonates, such as diethyl carbonate, amides, such as dimethylacetamide and also esters of aliphatic $C_1$ to $C_5$ carboxylic acids or aromatic carboxylic acids with aliphatic $C_1$ to $C_5$ alcohols, such as ethyl formate, n-propyl formate, isopropyl formate, n-butyl formate, isobutyl formate, tert-butyl formate, amyl formate, methyl acetate, ethyl acetate, n-propyl acetate, isopropyl acetate, n-butyl acetate, isobutyl acetate, tert-butyl acetate, amyl acetate, methyl propionate, ethyl propionate, n-propyl propionate, isopropyl propionate, n-butyl propionate, isobutyl propionate, tert-butyl propionate, amyl propionate, methyl butyrate, ethyl butyrate, n-propyl butyrate, isopropyl butyrate, n-butyl butyrate, isobutyl butyrate, tert-butyl butyrate, amyl butyrate, methyl valerate, ethyl valerate, n-propyl valerate, isopropyl valerate, n-butyl valerate, isobutyl valerate, tert-butyl valerate, amyl valerate, methyl benzoate or ethyl benzoate, and also lactones, such as butyrolactone, valerolactone, caprolactone, N-methylpyrrolidone or N-ethylpyrrolidone.

Preference, however, is given to selecting those protic organic solvents in which the free-radical initiators that are used in each case dissolve readily. Use is made in particular of those protic organic solvents in which not only the free-radical initiators but also the copolymers of the invention dissolve readily. Particular preference is given to selecting those protic organic solvents which additionally can be separated in a simple way, as for example by distillation, inert gas stripping and/or steam distillation, from the copolymer solution obtained. Preferred examples of such a protic organic solvent are methanol, ethanol, n-propanol or isopropanol, and also the corresponding alcohol/water mixtures. It is favorable if the solvent at atmospheric pressure (1 atm ≙ 1.013 bar absolute) has a boiling point≤140° C., frequently ≤125° C., and in particular≤100° C., or forms with water a low-boiling water/solvent azeotrope mixture. It will be appreciated that it is also possible to use a mixture of two or more solvents. With more particular preference, however, the polymerization takes place in an aqueous medium.

The amount of solvent when preparing the copolymer of the invention is 1 to 9900 parts by weight, preferably 100 to 1900 parts by weight, and with particular preference 150 to 900 parts by weight, based in each case on 100 parts by weight of total monomers.

In the course of the preparation of the copolymers of the invention it is possible, if appropriate, to include a portion or the total amount of solvent in the initial charge to the polymerization vessel. It is also possible, however, to meter in the total amount or, if appropriate, the remainder of solvent during the polymerization reaction. The total amount or, if appropriate, the remainder of solvent may in this context be metered into the polymerization vessel discontinuously in one or more portions or continuously with constant or changing volume flow rates. Advantageously a portion of the solvent is included in the initial charge to the polymerization vessel as a polymerization medium before the polymerization reaction is initiated, together with the total amount/portion of the monomers A and B and also, if appropriate, C, and the remainder is metered in together with the monomers A and B and also, if appropriate, C and with the free-radical initiator during the polymerization reaction.

Where the polymerization of the monomers A and B and also, if appropriate, C is carried out in an aqueous medium, it is common to use what are referred to as water-soluble free-radical initiators, which the skilled worker customarily uses in the context of free-radically initiated aqueous emulsion polymerization. Where, in contrast, the polymerization of the monomers is carried out in an organic solvent, it is usual to use what are called oil-soluble free-radical initiators, which the skilled worker customarily uses in the context of free-radically initiated solution polymerization. For the purposes of this specification, water-soluble free-radical initiators are understood to be all those free-radical initiators which at 20° C. under atmospheric pressure in deionized water have a solubility≥1% by weight, whereas oil-soluble free-radical initiators are understood to be all of those free-radical initiators which under the aforementioned conditions have a solubility<1% by weight. Frequently, water-soluble free-radical initiators have a water solubility under the aforementioned conditions≥2% by weight, ≥5% by weight or ≥10% by weight, while oil-soluble free-radical initiators frequently have a water solubility ≤0.9%, ≤0.8%, ≤0.7%, ≤0.6%, ≤0.5%, ≤0.4%, ≤0.3%, ≤0.2% or ≤0.1% by weight.

The water-soluble free-radical initiators in this case may for example be either peroxides or azo compounds. Peroxides which can be used are in principle inorganic peroxides, such as hydrogen peroxide or peroxodisulfates, such as the mono- or di-alkali metal or -ammonium salts of peroxodisulfuric acid, such as, for example, its mono- and di-sodium, -potassium or -ammonium salts, or organic hydroperoxides, such as alkyl hydroperoxides, examples being tert-butyl, p-menthyl or cumyl hydroperoxide. Azo compounds used are essentially 2,2'-azobis(2-(2-imidazolin-2-yl)propyl)dihydrochloride or 2,2'-azobis(amidinopropyl)dihydrochloride.

Examples of oil-soluble free-radical initiators include dialkyl and diaryl peroxides, such as di-tert-amyl peroxide, dicumyl peroxide, bis(tert-butylperoxyisopropyl)benzene, 2,5-bis(tert-butylperoxy)-2,5-dimethylhexane, tert-butyl cumene peroxide, 2,5-bis(tert-butylperoxy)-2,5-dimethyl-3-hexene, 1,1-bis(tert-butylperoxy)-3,3,5-trimethylcyclohexane, 1,1-bis(tert-butylperoxy)cyclohexane, 2,2-bis(tert-butylperoxy)butane or di-tert-butyl peroxide, aliphatic and aromatic peroxy esters, such as cumyl peroxyneodecanoate, 2,4,4-trimethylpentyl 2-peroxyneodecanoate, tert-amyl peroxyneodecanoate, tert-butyl peroxyneodecanoate, tert-amyl peroxypivalate, tert-butyl peroxypivalate, tert-amyl peroxy-2-ethylhexanoate, tert-butyl peroxy-2-ethylhexanoate, tert-butyl peroxydiethylacetate, 1,4-bis(tert-butylperoxy)cyclohexane, tert-butyl peroxyisobutanoate, tert-butyl peroxy-3,5,5-trimethylhexanoate, tert-butyl peroxyacetate, tert-amyl peroxybenzoate or tert-butyl peroxybenzoate, dialkanoyl and dibenzoyl peroxides, such as diisobutanoyl peroxide, bis(3,5,5-trimethylhexanoyl)peroxide, dilauroyl peroxide, didecanoyl peroxide, 2,5-bis(2-ethylhexanoylperoxy)-2,5-dimethylhexane or dibenzoyl peroxide, and also peroxycarbonates, such as bis(4-tert-butylcyclohexyl)peroxydicarbonate, bis(2-ethylhexyl)peroxydicarbonate, di-tert-butyl peroxydicarbonate, diacetyl peroxydicarbonate, dimyristyl peroxydicarbonate, tert-butyl peroxyisopropyl carbonate or tert-butyl peroxy-2-ethylhexyl carbonate. Examples of highly oil-soluble azo initiators used include 2,2''-azobis(isobutyronitrile), 2,2'-azobis(2-methylbutyronitrile), dimethyl 2,2'-azobisisobutyrate, 2,2'-azobis(2,4-dimethylvaleronitrile), and 4,4'-azobis(4-cyanopentanoic acid).

A preferred azo-type free-radical initiator used is a compound selected from the group comprising 2,2'-azobis(isobutyronitrile), 2,2'-azobis(2-methylbutyronitrile), dimethyl 2,2'-azobisisobutyrate, 2,2'-azobis(2,4-dimethylvaleronitrile), 4,4'-azobis(4-cyanopentanoic acid) or 2,2'-azobis(amidinopropyl)dihydrochloride. It is of course also possible to use mixtures of aforementioned free-radical initiators.

The amount of free-radical initiator used in preparing the copolymer of the invention is generally 0.01% to 10% by weight, preferably 0.1% to 5% by weight, and with particular preference 1% to 4% by weight, based in each case on the total monomer amount.

In the context of the preparation of the copolymer of the invention it is possible, if appropriate, to include a portion or the total amount of free-radical initiator in the initial charge to the polymerization vessel. It is also possible, however, to meter in the total amount or, if appropriate, the remainder of free-radical initiator during the polymerization reaction. The total amount or, if appropriate, the remainder of free-radical initiator may in that case be metered into the polymerization vessel discontinuously in one or more portions or continuously with constant or changing volume flow rates. With particular advantage the free-radical initiators are metered in during the polymerization reaction continuously with a constant volume flow rate—more particularly in the form of a solution of the free-radical initiator with the solvent used.

In one preferred embodiment the total amounts of the monomers A, B, and, if appropriate, C are included in an initial charge in a solvent, and a free-radical polymerization initiator is metered in discontinuously in two or more portions under polymerization conditions.

The copolymer of the invention advantageously has a K value in the range≥10 and ≤130 (determined at 25° C. in a 1% strength by weight aqueous solution). With particular advantage the copolymer has a K value in the range≥20 and ≤100. Setting the K value when preparing the copolymer of the invention is familiar to the skilled worker and is accomplished advantageously by means of free-radically initiated solution polymerization in the presence of free-radical chain transfer compounds, referred to as free-radical chain regulators. The determination of the K value as well is familiar to the skilled worker (see, for example, H. Fikentscher, "Systematik der Cellulosen aufgrund ihrer Viskosität in Lösung" in Cellulose-Chemie 13 (1932), pages 58 to 64 and also pages 71 to 74, or Encyclopedia of Chemical Technology, Vol. 21, $2^{nd}$ edition (1970), pages 427 and 428).

Examples of suitable free-radical chain regulators are isopropanol or organic compounds comprising sulfur in bonded form. These include, for example, mercapto compounds, such as mercaptoethanol, mercaptopropanol, mercaptobutanol, mercaptoacetic acid, mercaptopropionic acid, butyl mercaptan, and dodecyl mercaptan. Further free-radical chain regulators are familiar to the skilled worker. If the polymerization is carried out in the presence of free-radical chain regulators, it is common to use 0.01% to 10% by weight, based on the total monomer amount.

When preparing the copolymer of the invention it is possible to include at least one portion of the free-radical chain regulator in the initial charge in the polymerization medium and to add, if appropriate, the remainder to the polymerization medium, after the free-radical polymerization reaction has been initiated, this second addition taking place discontinuously in one portion, discontinuously in two or more portions, and also continuously with constant or changing volume flow rates.

By skilled variation of the nature and amount of the monomers A and B and also, if appropriate, C it is possible in accordance with the invention for the skilled worker to prepare copolymers which have a glass transition temperature or a melting point in the range from −60 to 270° C. In accordance with the invention advantageously the glass transition temperature of the copolymer is ≥40° C. and ≤250° C., and preferably ≥100° C. and ≤200° C.

The glass transition temperature, $T_g$, is the limit value of the glass transition temperature toward which said temperature tends with increasing molecular weight, according to G. Kanig (Kolloid-Zeitschrift & Zeitschrift für Polymere, Vol. 190, p. 1, equation 1). The glass transition temperature or the melting point is determined by the DSC method (differential scanning calorimetry, 20 K/min, midpoint measurement, DIN 53765).

According to Fox (T. G. Fox, Bull. Am. Phys. Soc. 1956 [Ser. II] 1, page 123 and in accordance with Ullmann's Encyclopädie der technischen Chemie, Vol. 19, page 18, 4th edition, Verlag Chemie, Weinheim, 1980) it is the case for the glass transition temperature of copolymers with no more than low degrees of crosslinking, in good approximation, that:

$$1/T_g = x^1/T_g^1 + x^2/T_g^2 + \ldots x^n/T_g^n,$$

where $x^1, x^2, \ldots x^n$ are the mass fractions of the monomers 1, 2, ... n, and $T_g^1, T_g^2, \ldots T_g^n$ are the glass transition temperatures of the polymers composed in each case only of one of the monomers 1, 2, ... n, in degrees Kelvin. The $T_g$ values for the homopolymers of the majority of monomers are known and are listed, for example, in Ullmann's Encyclopedia of Industrial Chemistry, 5$^{th}$ edition, Vol. A21, page 169, VCH Weinheim, 1992; further sources of glass transition temperatures of homopolymers include, for example, J. Brandrup, E. H. Immergut, Polymer Handbook, 1$^{st}$ ed., J. Wiley, New York 1966, 2$^{nd}$ ed., J. Wiley, New York 1975, and 3$^{rd}$ ed., J. Wiley, New York 1989).

The free-radically initiated polymerization takes place—depending on the free-radical initiator used—customarily at temperatures in the range from 40 to 180° C., preferably from 50 to 150° C., and more particularly from 60 to 110° C. As soon as the temperature during the polymerization reaction is above the boiling point of the solvent and/or one of the monomers A and B and also, if appropriate C, the polymerization is advantageously carried out under pressure (>1 atm absolute). The temperature and pressure conditions are familiar to the skilled worker or can be determined by him or her in a few routine experiments.

The copolymer of the invention can be prepared in the presence of air; advantageously, however, the polymerization takes place under low-oxygen or oxygen-free conditions, such as under inert gas, for example, such as nitrogen or argon.

The copolymer of the invention can be prepared in the customary polymerization apparatus. Use is made for this purpose, for example, of glass flasks (laboratory) or stirred tanks (technical scale) which are equipped with an anchor, blade, impeller, cross-arm, MIG or multistage impulse countercurrent stirrer. Particularly in the case of polymerization in the presence of only small amounts of solvent it may also be advantageous to carry out the polymerization in customary single-screw or twin-screw (co- or counter-rotating) kneader reactors, such as those from List or Buss SMS, for example.

Where the copolymer of the invention is prepared in an organic solvent, the organic solvent is in general removed at least partly, advantageously to an extent of ≥50% by weight or ≥90% by weight, and with particular advantage completely, and the copolymer is taken up in water, advantageously in deionized water. The corresponding processes are familiar to the skilled worker. Thus, for example, the replacement of the solvent by water may be carried out by distilling off the solvent and replacing it by water under atmospheric pressure, for example, or at subatmospheric pressure (<1 atm absolute), at least partly, advantageously completely, in one or more stages. Frequently it may be advantageous to remove the solvent from the solution by introducing steam and at the same time replacing it by water. This is especially the case when the organic solvent has a certain steam volatility.

Particularly advantageous copolymers of the invention are those which at 20° C. and 1 atm (absolute) have a solubility≥100 g, preferably≥300 g, and with particular preference≥500 g per 1000 g of deionized water. Frequently the copolymers exhibit unlimited solubility with deionized water.

In accordance with the invention the copolymers of the invention can be present in the form of copolymer powders [obtainable, for example, from aqueous copolymer solutions by freeze-drying, roller drying or spray-drying] or in the form of solutions in aqueous media or in organic solvents, and inventively used in this form. It is advantageous to use copolymer powders or solutions of the copolymer of the invention in an aqueous medium. Use is made in particular of the copolymers of the invention in the aqueous medium in which the polymerization of the copolymers was carried out, or which was obtained following replacement of the organic solvent by water.

The copolymers obtainable by the method of the invention act on the one hand as thickeners in an aqueous medium and on the other hand are capable of forming films which are water-soluble or, following UV irradiation, water-insoluble. They are therefore employed more particularly in cosmetic and pharmaceutical preparations, in the capacity, for example, of additives or vehicles in hair lacquer, hairsetting agents or hairspray, in cosmetic preparations for the skin, as skin adhesion gels, or as immunochemicals, such as catheter coatings. Specific pharmaceutical applications of the copolymers of the invention comprise in particular their use as wet or dry binders, matrix retardants or coating retardants (for slow-release administration forms), instant-release coatings, and pan-coating assistants. The copolymers of the invention can be used, furthermore, as auxiliaries for agrochemistry, as for example for seed coating or for soil-release fertilizer formulations, or as auxiliaries in the production of fish-feed granules.

On account of the high dispersing action of the copolymers of the invention, for both organic and inorganic pigments, they are suitable as rust preventatives or rust removers from metallic surfaces, as scale inhibitors or scale removers, as dispersants in dye pigment dispersions, such as in printing inks, for example. In this context reference may also be made to the use of the copolymers of the invention for ink-jet recording media, ink pen pastes and ballpoint pen pastes.

Also of interest from the standpoint of technical applications is the high propensity of the copolymers of the invention to form complexes with further organic compounds, as for example with lower hydrocarbons, phenols, tannins or various antioxidants, with enzymes and proteins, and also with other organic polymers. Furthermore, the copolymers of the invention are capable of forming complexes with inorganic compounds, particularly with hydrogen peroxide, metals or metal salts. Accordingly the copolymers of the invention can be used with advantage to remove tannins, phenols, proteins or polyvalent cations from aqueous medium, in ion exchangers, for stabilizing hydrogen peroxide, in disinfectants, for example, or for stabilizing antioxidants, in preservatives, for example. The copolymers of the invention can be used, furthermore, for stabilizing metal colloids. Reference may also be made in this context to the use of the copolymers of the invention for producing noble metal crystallization nuclei for the precipitation of silver, and also as stabilizers for silver halide emulsions.

The copolymers of the invention are additionally suitable for modifying surface and interface properties. They can therefore be employed, for example, to hydrophilicize surfaces, and hence can be used as textile assistants, such as, for example, as exhaust assistants and leveling assistants in textile coloring procedures or as brightening agents in textile printing processes. On account of the modifying effect for surfaces, the copolymers of the invention can be used to coat organic and inorganic substrates, such as for polyolefins, for glass, and for glass fibers, for example. Reference may also be made in this context to the use of the copolymers of the invention as auxiliaries in the recovery of oil from oily water, as auxiliaries in the extraction of crude oil and natural gas, and also for crude-oil and natural-gas transport. Moreover, the copolymers of the invention find use as auxiliaries in the cleaning of wastewater, either as flocculating assistants or in the context of the removal of paint residues and oil residues from wastewater. The copolymers of the invention can be used, too, as phase transfer catalysts and as solubility improvers.

The copolymers of the invention find use, furthermore, in the coloring of polyolefins, as color transfer inhibitors in detergents, as color mixing inhibitors for photographic diffusion transfer materials, as adhesion promoters for dyes, as auxiliaries for lithography, for photoimaging, for the diazotype process, as auxiliaries for metal casting and metal hardening, as auxiliaries in metal quenching baths, as auxiliaries in gas analysis, as a constituent in ceramic binders, as a paper assistant for specialty papers, as a binder in paper coating slips, and as a binder constituent in plaster bandages.

The copolymers of the invention are suitable, furthermore, as proton conductors and can be used in electrically conducting layers, as for example in charge transfer cathodes, as solid electrolytes, in solid batteries, for example, such as lithium batteries in particular. From the copolymers of the invention it is also possible to produce contact lenses, synthetic fibers, air filters, e.g., cigarette filters, or membranes. In addition the copolymers of the invention find use in heat-resistant layers, heat-sensitive layers, and heat-sensitive resistors.

The copolymers of the invention are suitable with particular advantage for applications where photochemical crosslinking of the copolymers is of advantage. These advantages may be, for example, attachment to surfaces or the generation of crosslinked or partly crosslinked gels. Accordingly the copolymers of the invention and/or formulations which comprise such copolymers are suitable with advantage for the use of coating retardants and gel formers, especially for slow-release administration forms of drugs, for seed coating, for photochemically crosslinkable adhesives and adhesive gels, especially skin adhesion gels, for ink-jet recording media, printing inks, coating materials, such as for fibers, films, glass, and surfaces of any kind, for example, for the photochemical fixing of the copolymers in membranes, especially in polymer membranes, and more particularly for rendering membrane surfaces hydrophilic permanently and in such a way that the hydrophilicization cannot be removed by washing.

The copolymers of the invention find use with particular advantage as coating materials or dressings for seed, as binders or coating materials for pharmaceuticals, as film formers or thickeners in cosmetics formulations, as an adhesive component in adhesives or glue sticks, as coating materials for paper, glass fibers or medical catheters, as a binder in the production of paints and varnishes, or for pore formation in and permanent hydrophilicization of polymer membranes.

Films of the copolymers of the invention can be produced by introducing copolymer solutions onto substrates or into substrates, thereafter removing the solvents, as for example by heating, under atmospheric pressure or under subatmospheric pressure, and, in the process, the copolymers filming in the course of this procedure at a temperature which is higher than the glass transition temperature or the corresponding film formation temperature of the copolymers, and thereafter irradiating the resulting copolymer films with UV light, to form crosslinked copolymer films having new, improved properties, such as, for example, reduced water solubility, increased hardness or improved extension properties. UV sources which can be used are the customary sources, examples being low, medium or high pressure mercury vapor lamps, which may have outputs of 20 to 100 J/sec×cm$^2$. Lamps with a higher output generally permit more rapid crosslinking. In certain cases, in the course of the crosslinking irradiation process, residual solvent may be removed at the same time by virtue of the IR component of the lamps.

Where the copolymers of the invention are used for pore formation in and permanent hydrophilicization of polymer membranes, use is made in particular of those synthetic polymers which have good solubility in polar, aprotic solvents but have only very little solubility, or none, in aqueous media, such as, for example, polysulfones, such as polyethersulfones, especially polymeric aromatic polysulfones, which are sold, for example, under the trade names Ultrason® by BASF SE, and Radel® and Udel® by Solvay GmbH. In addition, for example, polyvinylidene fluoride (PVDF), which is sold, for example, under the trade name Kynar® PVDF by Arkema S. A., Dyneon® PVDF by Dyneon GmbH or Solef® PVDF by Solvay GmbH, and also suitable polycarbonates, polyvinyl chloride, polyacrylates, polyethers, cellulose derivatives, polysorbates, and polyurethanes, are employed to produce the membranes. The membranes are produced by dissolving the synthetic polymer in question together with a copolymer of the invention in a polar aprotic solvent, especially dimethylformamide, dimethyl sulfoxide, dimethylacetamide, N-methylpyrrolidone or mixtures thereof, and carrying out precipitation from these solutions under suitable conditions, to form porous polymer membranes.

In these cases the amounts are chosen such that in the completed polymer solution the amount of synthetic polymer is generally 10% to 25%, preferably 12% to 20%, and more particularly 14% to 18%, by weight, while the amount of copolymer of the invention is generally 0.1% to 15%, preferably 1% to 10%, and more particularly 2% to 8%, by weight. Besides the copolymer of the invention it is also possible to use other water-soluble copolymers, such as vinylpyrrolidone homopolymers or copolymers, for example.

The polymer solution is generally also filtered and then introduced in a manner familiar to the skilled worker, as for example by means of what is referred to as a precipitation nozzle, into a precipitation medium (in this regard see, for example, K. Ohlrogge, K. Ebert, Membranen: Grundlagen, Verfahren and industrielle Anwendungen, Wiley-VCH-Verlag, Weinheim, 2006).

In this context the precipitation medium is generally composed of a mixture of one of the aforementioned polar aprotic solvents with water, which initiates the precipitation of the synthetic polymer, but also partly dissolves out the hydrophilic copolymer to form a porous membrane. It will be appreciated that the precipitation medium may comprise customary additives. Depending on the way in which the polymer solution is introduced into the precipitation medium, flat membranes and hollow-fiber membranes are obtained preferentially.

Subsequent irradiation of the resulting porous membranes with UV light subjects the copolymer of the invention that has remained on the membrane surface to a crosslinking reaction, as a result of which the crosslinked copolymer of the invention becomes insoluble in water and so attaches permanently to the membrane surface, while the hydrophilic properties of the crosslinked copolymer of the invention undergo virtually no change.

The following, nonlimiting examples are intented to illustrate the invention.

I. Preparation of the Polymers

Polymer A

A 2 l four-neck flask equipped with anchor stirrer, reflux condenser, and nitrogen inlet was charged at 20 to 25° C. (room temperature) and under a nitrogen atmosphere with 410 g of N-vinylpyrrolidone, 870 g of deionized water, 1.2 g of 25% strength by weight aqueous ammonia, and 11.5 g of a 35% strength by weight solution of 4-[(benzoylphenoxy)carboxy]butyl acrylate in methyl ethyl ketone, and the resulting reaction mixture was heated to 75° C. under a nitrogen atmosphere. When that temperature was reached, the reaction mixture was admixed in one go with 10.0 g of a 30% strength by weight aqueous solution of hydrogen peroxide and with 0.5 g of a 0.01% strength by weight aqueous solution of copper(II) chloride. Beginning at the same time, 2.0 g of 25% strength by weight aqueous ammonia were metered continuously into the polymerization mixture over the course of 35 minutes, after which the polymerization mixture was heated to 85° C. and stirred at that temperature for 25 minutes. After that, 1.7 g of the 30% strength by weight aqueous solution of hydrogen peroxide and 0.2 g of the 0.01% strength by weight aqueous solution of copper(II) chloride were added in one go and the polymerization mixture was stirred at 85° C. for an hour. Thereafter, 2.9 g of the 30% strength by weight aqueous solution of hydrogen peroxide and 0.2 g of the 0.01% strength by weight aqueous solution of copper(II) chloride were added in one go, and the polymerization mixture was stirred at 85° C. for a further hour and then cooled to room temperature. This gave a polymer solution having a solids content of 32% by weight. The resulting polymer had a K value of 29.

The solids content was determined in general by drying a defined amount of the aqueous polymer solution (approximately 1 g) to constant weight in a drying cabinet in an aluminum crucible having an internal diameter of approximately 5 cm at 120° C. (for about 2 hours). Two separate measurements were carried out in each case. The figures reported in the examples represent the average of the two measurement results in each case.

The determination of the K value by the method of Fikentscher was made generally at 25° C. using an instrument from Schott, Mainz (capillary: micro-Ostwald; type: MO-Ic). The aqueous copolymer solutions obtained were mixed with deionized water so that the resulting homogeneous solutions had a polymer content of 1.0% by weight.

Polymer B

A 2 l four-neck flask equipped with anchor stirrer, reflux condenser, and nitrogen inlet was charged at room temperature and under a nitrogen atmosphere with 200 g of N-vinylpyrrolidone and 950 g of deionized water, and the pH was adjusted to 8.5 using 25% strength by weight aqueous ammonia. Subsequently the aqueous initial charge was heated to 75° C. When a temperature of 70° C. was reached, 0.5 g of a 25% strength by weight solution of 2,2'-azobis(2-methylbutyronitrile) in isopropanol was added in one go and, beginning simultaneously, a mixture of 43.6 g of N-vinylpyrrolidone and 6.4 g of a 35% strength by weight solution of 4-[(benzoylphenoxy)carboxy]butyl acrylate in methyl ethyl ketone was metered in continuously over the course of 30 minutes. Thereafter the polymerization mixture was left with stirring at 75° C. for 30 minutes, after which a further 0.5 g of the isopropanolic solution of 2,2'-azobis(2-methylbutyronitrile) was added in one go, the mixture was left with stirring at 75° C. for a further 60 minutes, a further 2.0 g of the isopropanolic solution of 2,2'-azobis(2-methylbutyronitrile) were added in one go, and the mixture was left with stirring at 75° C. for a further 30 minutes, and then the polymerization mixture was heated to 90° C. and left at that temperature for 2 hours. The resulting copolymer solution was adjusted to a pH of 3 using formic acid, stirred for 30 minutes, then neutralized using the 25% strength by weight aqueous ammonia, and afterward the polymer solution obtained was stripped with steam until approximately 500 ml of liquid had distilled from the polymerization vessel into the distillation receiver. Subsequently the resulting polymer solution was cooled to room temperature. The polymer solution thus obtained had a solids content of 21% by weight. The K value was found to be 93.

Polymer C

Polymer C was prepared as for polymer B, with the difference that 2.4 g of 4-vinyloxybenzophenone were added instead of 4-[(benzoylphenoxy)carboxy]butyl acrylate. The resulting polymer solution had a solids content of 23% by weight. The K value was found to be 90.

Polymer D

Polymer D was prepared as for polymer B, with the difference that 2.4 g of 2-(acryloyloxy)ethyl 4-(4-chlorobenzoyl)benzoate (Uvecryl® P36 from Sigma-Aldrich Chemie GmbH) were added instead of 4-[(benzoylphenoxy)carboxy]butyl acrylate. The resulting polymer solution had a solids content of 25% by weight. The K value was found to be 95.

Polymer E

Comparative Example 1

Polymer E was prepared in the same way as for the preparation of polymer A, with the difference that no 4-[(benzoylphenoxy)carboxy]butyl acrylate was used. The resulting polymer solution had a solids content of 31% by weight. A K value of 31 was found.

Polymer F

Comparative Example 2

Polymer F was prepared in the same way as for the preparation of polymer B, with the difference that no 4-[(benzoylphenoxy)carboxy]butyl acrylate was used. The resulting polymer solution had a solids content of 19% by weight. A K value of 93 was found.

II. Studies of the Solubility of the Polymer Films

All of the aforementioned polymer solutions were adjusted with deionized water to a solids content of 15% by weight. Then portions of the polymer solutions of polymers E and F were freeze-dried, subsequently taken up in isopropanol to form a 15% strength by weight alcoholic solution, and admixed with 1% by weight in each case of the following commercially available photoinitiators Irgacur® 500 and Darocur® 1173 (commercial products from Ciba Spezialitätenchemie, Lampertheim) and also of benzophenone, based in each case on the solids content of the polymer solutions; these preparations were mixed homogeneously by stirring for 5 minutes. Thereafter the polymer solutions of polymers A to F, and also the polymer solutions of polymers E and F additized with the aforementioned photoinitiators, in two series, were applied with a film thickness of 500 μm to grease-free glass plates measuring 8×30 cm, and the coated glass plates thus obtained were dried in a controlled-climate chamber at 23° C. and 50% relative humidity for 24 hours. The polymer films obtained on the glass plates had a film thickness of approximately 50 μm. After the drying process, a series of the coated glass plates was irradiated using a UV exposure unit from IST Strahlentechnik Metz GmbH, comprising two eta plus M400-U2HC lamps (UV emitters in the wavelength range from 180 to 450 nm) with a radiation intensity of 3700 mJ/cm². After that, the coated glass plates of both series were immersed vertically in deionized water at room temperature for 5 minutes, after which the coated glass plates were dabbed dry with a cotton cloth and subjected to visual evaluation with respect to their coating. The results obtained are listed in the table below:

| Polymer | Condition of film after water bath | |
| --- | --- | --- |
|  | unirradiated | irradiated |
| A | dissolved | undissolved |
| B | dissolved | undissolved |
| C | dissolved | undissolved |
| D | dissolved | undissolved |
| E | dissolved | dissolved |
| E + Irgacur 500 | dissolved | dissolved |
| E + Darocur 1173 | dissolved | dissolved |
| E + benzophenone | dissolved | dissolved |
| F | dissolved | dissolved |
| F + Irgacur 500 | dissolved | dissolved |
| F + Darocur 1173 | dissolved | dissolved |
| F + Benzophenon | dissolved | dissolved |

From the results it is clearly apparent that the copolymers of the invention (polymers A to D), after irradiation with UV light, formed water-insoluble, in some cases easily swollen films, whereas the corresponding polymer films without UV irradiation dissolved completely in water. In contrast, polyvinylpyrrolidones (polymers E and F), which comprised no monomers of the general formula (I) in copolymerized form, or to which UV photoinitiators had been admixed subsequently as separate components, formed polymer films of only good water solubility even after corresponding UV irradiation.

The invention claimed is:
1. A copolymer, consisting essentially of, in copolymerized form:
   (A) 0.01% to 20% by weight of at least one ethylenically unsaturated compound of formula (I),

$$R—(C=O)—R^1 \quad (I),$$

wherein
   R is a straight-chain $C_1$-$C_4$ alkyl radical, a branched, optionally substituted $C_3$ or $C_4$ alkyl radical, an aryl radical, or a $R_1$, and
   $R^1$ is

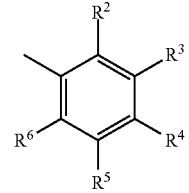

wherein $R^2$ to $R^6$ are each, independently, hydrogen, alkyl, aryl, OH, $OCH_3$, $OC_2H_5$, SH, $SCH_3$, $SC_2H_5$, F, Cl, Br, CN, $CO_2H$, $CO_2$alkyl, $CO_2$aryl, $CF_3$, $N(alkyl)_2$, $N(alkyl)(aryl)$, $N(aryl)_2$, $N^+(alkyl)_3A^-$, $N^+H(alkyl)_2A_-$, wherein $A^-$ is an anion of an acid, and at least one but not more than three of the radicals $R^2$ to $R^6$ is or are selected from the group consisting of $$—O—C(O)—O—X—NY—C(O)—CY=CH_2, \quad (II)$$

$$—O—\underset{\underset{O}{\|}}{C}—O—X—Z—\underset{H}{C}=CH_2, \quad (III)$$

$$—Z—\underset{Y}{C}=CH_2, \quad (IV)$$

$$—\underset{\underset{O}{\|}}{C}—O—X—Z—\underset{\underset{O}{\|}}{C}—\underset{Y}{C}=CH_2, \text{ and} \quad (V)$$

$$—\underset{\underset{O}{\|}}{C}—O—X—Z—\underset{H}{C}=CH_2, \quad (VI)$$

wherein
   X is a divalent, optionally substituted alkylene radical $—(CH_2)_m—$,
   a radical

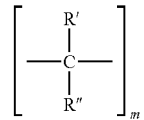

with m=1 to 10, wherein R' and R" are each independently hydrogen, alkyl, aryl, $CO_2H$, $CO_2CH_3$ or $CO_2C_2H_5$, a perfluorinated alkylene radical $—(CF_2)_m—$ with m=1 to 10, an oxaalkylene radical of a formula —(CH$_2$)$_n$—O—(CH$_2$)$_p$—, a perfluorinated oxaalkylene radical of a formula —(CF$_2$)$_n$—O—(CF$_2$)$_p$— with n=1 to 5 and p=1 to 5, an optionally perfluorinated polyoxaalkylene radical having 2 to 20 oxygen atoms which are joined to one another via at least one —CH$_2$—, —CF$_2$—, or —CH$_2$—CH(CH$_3$)— group, or are an alkylene radical of a formula —(CH$_2$)$_a$—O—CO—O(CH$_2$)$_b$—, —(CH$_2$)$_a$—O—CO—NH—(CH$_2$)$_b$—, —(CH$_2$)$_a$—NH—CO—O—(CH$_2$)$_b$—, —(CH$_2$)$_a$—CO—(CH$_2$)$_b$—, or —(CH$_2$)$_a$—O—CO—(CH$_2$)$_b$— with a=1 to 10 and b=1 to 10, a phenylene radical which is optionally substituted by alkyl, OH, OCH$_3$, OC$_2$H$_5$, SH, SCH$_3$, SC$_2$H$_5$, Cl, F, N(alkyl)$_2$, or N(CH$_3$)C$_6$H$_5$ in at least one of an o-, m-, and p-position, a cycloalkylene radical having 5 to 10 carbon atoms, or a (bis)methylenecycloalkylene radical having 6 to 12 carbon atoms, Y is hydrogen, alkyl, or aryl, and Z is O or NY, or, if R is an aryl radical, one of the radicals R$^2$ or R$^6$ is optionally a sulfur atom which connects the aryl radical R in an o-position to R$^1$;

(B) 80% to 99.99% by weight of at least one N-vinyllactam of formula (VII),

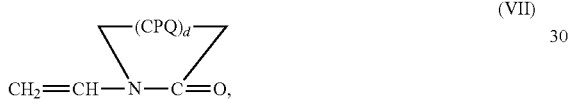
(VII)

wherein

P and Q are independently of one another are at least one of hydrogen and alkyl, and d is an integer from 2 to 8.

2. The copolymer of claim 1, consisting essentially of
0.1% to 5% by weight of (A) and
95% to 99.9% by weight of (B).

3. The copolymer of claim 1, wherein the (B) N-vinyllactam of formula (VII) comprises at least one of N-vinylpyrrolidone and N-vinylcaprolactam.

4. The copolymer of claim 1, comprising, as (A), a compound wherein
R is phenyl,
R$^2$, R$^3$, R$^5$, and R$^6$ are hydrogen, and
R$^4$ is a group of formula (IV) wherein
Y is hydrogen, and
Z is O.

5. The copolymer of claim 1, comprising, as (A), a compound wherein
R is p-chlorophenyl,
R$^2$, R$^3$, R$^5$, and R$^6$ are hydrogen, and
R$^4$ is a group of formula (V) wherein
X is (CH$_2$)$_2$,
Y is hydrogen, and
Z is O.

6. A process for preparing the copolymer of claim 1, comprising free-radical polymerization of (A) with (B).

7. The process of claim 6, wherein complete amounts of (A) and (B) are introduced in a solvent, and
a free-radical polymerization initiator is metered in under polymerization conditions.

8. A coating material or dressing for seed, a binder or coating material for a pharmaceutical, a film-former or thickener in a cosmetics formulation, an adhesive component in an adhesive or glue stick, a coating material for paper, a glass fiber or medical catheter, a binder for producing a paint or varnish, or a polymer membrane, comprising the copolymer of claim 1.

9. A method of at least one of coating a substrate and modifying a substrate, the method comprising:
introducing a solution of the copolymer of claim 1 onto a substrate or into a substrate; thereafter
removing solvent under atmospheric pressure or under subatmospheric pressure, thereby causing the copolymer to form a resulting copolymer film; and thereafter
irradiating the resulting copolymer film with UV light.

10. The copolymer of claim 1, consisting of
0.1% to 5% by weight of (A) and
95% to 99.9% by weight of (B).

11. The copolymer of claim 2, wherein the N-vinyllactam of formula (VII) comprises at least one of N-vinylpyrrolidone and N-vinylcaprolactam.

12. The copolymer of claim 2, comprising, as (A), a compound wherein
R is phenyl,
R$^2$, R$^3$, R$^5$, and R$^6$ are hydrogen, and
R$^4$ is a group of formula (IV) wherein
Y is hydrogen, and
Z is O.

13. The copolymer of claim 3, comprising, as (A), a compound wherein
R is phenyl,
R$^2$, R$^3$, R$^5$, and R$^6$ are hydrogen, and
R$^4$ is a group of formula (IV) wherein
Y is hydrogen, and
Z is O.

14. The copolymer of claim 2, comprising, as (A), a compound wherein
R is p-chlorophenyl,
R$^2$, R$^3$, R$^5$, and R$^6$ are hydrogen, and
R$^4$ is a group of formula (V) wherein
X is (CH$_2$)$_2$,
Y is hydrogen, and
Z is O.

15. The copolymer of claim 3, comprising, as (A), a compound wherein
R is p-chlorophenyl,
R$^2$, R$^3$, R$^5$, and R$^6$ are hydrogen, and
R$^4$ is a group of formula (V) wherein
X is (CH$_2$)$_2$,
Y is hydrogen, and
Z is O.

16. A process for preparing the copolymer of claim 2, comprising free-radical polymerization of (A) and (B).

17. A process for preparing the copolymer of claim 3, comprising free-radical polymerization of (A) and (B).

* * * * *

UNITED STATES PATENT AND TRADEMARK OFFICE
CERTIFICATE OF CORRECTION

PATENT NO.        : 8,629,227 B2                                      Page 1 of 1
APPLICATION NO.   : 13/133171
DATED             : January 14, 2014
INVENTOR(S)       : Frank Fischer et al.

It is certified that error appears in the above-identified patent and that said Letters Patent is hereby corrected as shown below:

On the title page, Item (73), the Assignee's Information is incorrect. Item (73) should read:

--(73)   Assignee:   BASF SE, Ludwigshafen, (DE)--

Signed and Sealed this
Thirteenth Day of May, 2014

Michelle K. Lee
*Deputy Director of the United States Patent and Trademark Office*